United States Patent [19]

Lee et al.

[11] Patent Number: 5,808,735
[45] Date of Patent: Sep. 15, 1998

[54] METHOD FOR CHARACTERIZING DEFECTS ON SEMICONDUCTOR WAFERS

[75] Inventors: Ken K. Lee, Los Altos; Ke Han, San Francisco; Lakshman Srinivasan, San Jose; Bruce W. Worster, Saratoga, all of Calif.

[73] Assignee: Ultrapointe Corporation, San Jose, Calif.

[21] Appl. No.: 756,420

[22] Filed: Nov. 26, 1996

Related U.S. Application Data

[63] Continuation-in-part of Ser. No. 497,162, Jun. 30, 1995, abandoned, which is a continuation-in-part of Ser. No. 80,014, Jun. 17, 1993, Pat. No. 5,479,252.

[51] Int. Cl.$^6$ ..................................................... G01N 21/00
[52] U.S. Cl. .................... 356/237; 356/369; 250/559.42; 250/559.48
[58] Field of Search .................................. 356/237, 369; 250/559.42, 559.48

Primary Examiner—Frank G. Font
Assistant Examiner—Reginald A. Ratliff
Attorney, Agent, or Firm—Skjerven, Morrill, MacPherson, Franklin & Friel LLP

[57] ABSTRACT 10A method is described for detecting and characterizing defects on a test surface of a semiconductor wafer. A three-dimensional image of the test surface is aligned and compared with a three-dimensional image of a defect-free reference surface. Intensity differences between corresponding pixels in the two images that exceed a predefined threshold value are deemed defect pixels. According to the method, the pixels of the reference image are grouped according to their respective z values (elevation) to identify different physical layers of the reference surface. Because different surface layers can have different image properties, such as reflectance and image texture, the groups of pixels are analyzed separately to determine an optimal threshold value for each of the groups, and therefore for each layer of the reference surface.

14 Claims, 7 Drawing Sheets

METHOD FOR CHARACTERIZING DEFECTS ON SEMICONDUCTOR WAFERS

CROSS-REFERENCES TO RELATED APPLICATIONS

The present application is a continuation-in-part of commonly owned application Ser. No. 08/497,162 now abandoned, filed on 30 Jun. 1995, entitled "Method for Characterizing Defects on Semiconductor Wafers," by Bruce W. Worster and Ken K. Lee, which is a continuation-in-part of commonly owned application Ser. No. 08/080,014, filed on 17 Jun., 1993, now U.S. Pat. No. 479,252entitled "Laser Imaging System For Inspection and Analysis of Sub-Micron Particles," by Bruce W. Worster, Dale E. Crane, Hans J. Hansen, Christopher R. Fairley, and Ken K. Lee. The present application is related to the following commonly owned, copending U.S. patent applications:

1. "A Method and Apparatus for Performing an Automatic Focus Operation," by Timothy V. Thompson, Christopher R. Fairley, and Ken K. Lee, application Ser. No. 08/183,536, filed on 18 Jan., 1994;
2. "A Method and Apparatus for Automatic Focusing of a Confocal Laser Microscope," by Christopher R. Fairley, Timothy V. Thompson, and Ken K. Lee, application Ser. No. 08/373,145, filed on 17 Jan., 1995;
3. "Surface Extraction from a Three-Dimensional Data Set," by Ken K. Lee, application Ser. No. 08/079,193, filed on 17 Jun., 1993, now Statutory Invention Registration No. H1530;
4. "Surface Data Processor," by Abigail A. Moorhouse, Christopher R. Fairley, Phillip R. Rigg, and Alan Helgesson, application Ser. No. 08/198,751, filed on 18 Feb. 1994;
5. "Automated Surface Acquisition For a Confocal Microscope," by Ken Kinsun Lee, application Ser. No. 08/483,234, filed on 7 Jun. 1995; and
6. "Method for Forecasting the Effects of Defects on Semiconductor Wafers," by Ken K. Lee, Bruce W. Worster, and John M. Scott, application Ser. No. 08/730,238, filed on 30 Jun. 1995.

These applications are incorporated herein by this reference.

BACKGROUND

Defects, such as structural flaws, process residues, and external contamination, occur during the production of semiconductor wafers. Defects are typically detected by a class of instruments called defect scanners. Such instruments automatically scan wafer surfaces and detect optical anomalies using a variety of techniques. The locations of these anomalies with respect to the pattern of semiconductor devices on the wafer surface are recorded. This information, or "defect map," is stored in a computer file and sent to a defect review station.

Using the defect map to locate each defect, a human operator observes each defect under a microscope and classifies each defect according to type (e.g., particle, pit, scratch, or contaminant). Information gained from this process is used to correct the source of defects, and thereby improve the efficiency and yield of the semiconductor production process. Unfortunately, people are relatively slow and are quickly fatigued by the highly repetitive task of observing and classifying defects.

Methods of automatically classifying defects, collectively known as Automatic Defect Classification or "ADC," have been developed to overcome the disadvantages of manual defect classification. (ADC alternatively stands for Automatic Defect Characterization.) In conventional ADC, review stations are automated to load a wafer that has been mapped for defect location by a defect scanner. Once the mapped wafer is loaded, the review station:

1. positions the wafer to image the site of a defect, as indicated by the defect map;
2. focuses on the site of the defect;
3. captures a digital image of the site using a digital TV camera;
4. processes and analyzes the captured image of the site to locate the defect; and
5. further analyzes the data to classify the defect.

The above process is repeated for each defect (or a predetermined subset of defects) on the wafer. The wafer is then unloaded and the process is repeated for another wafer. By eliminating a fatiguing and highly repetitive task, such automated review stations reduce labor costs and provide improved consistency and accuracy over human operators.

Conventional ADC systems capture a white-light microscope image as an array A representing a two-dimensional image. The image is an x-y array of n by m pixels, where typical values might be n=640, m=480, or n=512, m=512. This array may be represented as:

A(x, y, Ir, Ig, Ib), where x and y are pixel coordinates, and Ir, Ig, and Ib represent the intensities of the red, green, and blue image components, respectively. Of course, grey scale images may also be used, as may other color schemes, such as those of the YUV and YIQ commercial standard formats. In the case of a grey scale image, a single intensity parameter is used.

In addition to imaging the defect site, at least one reference image $A_{ref}$ is also stored. The reference image may be a previously stored data-base image of a corresponding known-good area of the same or a similar die on the same or on a similar wafer, or it may be a specific image taken from, e.g., an adjacent die. The reference image is compared with the image containing the defect. Differences measured between the two images indicate the location and extent of the defect.

Once a defect area is identified, a set of primitives representing the defect is used to develop a set of defect parameters, each defect parameter representing a single feature of the defect. For example, one defect parameter may represent the area of the defect and another the shape of the defect. Moreover, characteristics of the area defined by the defect boundaries may be used to derive additional defect parameters. For example, the defect area may be analyzed for average intensity, variations in intensity from one pixel to the next or within a small region ("texture"), color, or color coordinates. The defect parameters are conventionally expressed in a normalized form so that they run from, e.g., 0 to 1 or −1 to 1. A defect-parameter vector is then defined by these parameters.

The defect-parameter vector is compared, using conventional fuzzy logic techniques, with typical vectors for each known type of defect. Based on this comparison, the ADC system classifies the defect and estimates the probability that the selected characterization is accurate. For further discussion of conventional ADC techniques, see the IBM technical disclosure entitled "Automated Classification of Defects in Integrated Circuit Manufacturing," by Frederick Y. Wu, et al., which is incorporated herein by this reference.

Conventional ADC systems work well to detect, characterize, and classify defects. However, if the comparison of test and reference images is too sensitive, many test surfaces are incorrectly deemed defective due to normal differences between test and reference surfaces and due to different image characteristics resulting from, for example, the test and reference images being imaged at different focal points or intensities. For this reason, corresponding pixels are compared using an intensity-error threshold: if the difference between the image intensities of corresponding test and reference pixels does not exceed the error threshold, then the difference is not deemed the result of a defect.

The use of an error threshold decreases the instances of false defect detection. Unfortunately, it also decreases the sensitivity with which defects are detected. Accordingly, great care is taken to optimize the error threshold for a given image comparison. Still, there remains a demand for error-threshold optimization methods that further improve defect detection.

SUMMARY

The present invention is directed, in part, to an improved error-threshold optimization method. According to the method, a reference surface is imaged in three dimensions. The reference image is described as an array of pixels each having a unique x-y coordinate, a z coordinate, and an intensity value I.

Different physical layers of a given surface are typically of different types of materials, and therefore exhibit different image properties. For example, a particular layer on a semiconductor substrate may be of pure silicon, silicon dioxide, metal, or photoresist. In accordance with an embodiment of the invention, the pixels representing a reference surface are grouped by elevation (i.e., Z) to identify separate physical layers of the reference surface. The image properties of different layers are then separately analyzed to establish an optimum intensity error threshold for each physical layer.

A system in accordance with the present invention detects defects on a test surface by aligning and comparing an image of the test surface with the reference image. Intensity differences between corresponding pixels in the two images that exceed the optimum intensity error threshold for that pixel pair are deemed defect pixels. The defect pixels are then collected to define a high level defect. In accordance with one embodiment of the invention, the speed of collecting defect pixels is increased using novel dilation and erosion techniques.

BRIEF DESCRIPTION OF THE FIGURES

These and other features, aspects, and advantages of the present invention will become better understood with regard to the following description, appended claims, and accompanying figures, where:

DETAILED DESCRIPTION

Figure 1:
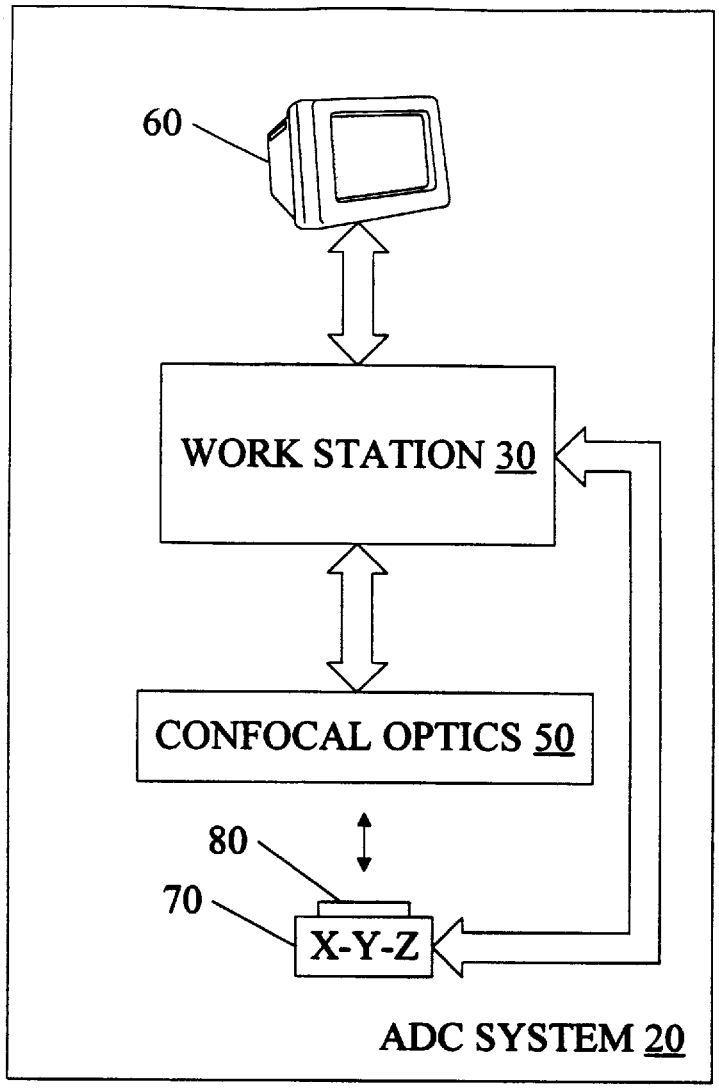
FIG. 1 is a block diagram of a conventional defect scanner 10 connected to an ADC system 20.

FIG. 1 is a block diagram of an system 20. In accordance with the present invention, ADC system 20 separates an image of a reference surface into constituent layers by grouping pixel data by elevation (i.e., Z). Different layers of a given surface are typically of different types of materials, and therefore exhibit different image properties. For example, different layers on semiconductor substrates may be layers of pure silicon, silicon dioxide, metals, or photoresist. ADC system 20 takes advantage of the different image properties of different layers by separately analyzing the image properties of different layers to establish an optimal error threshold for each layer. ADC system 20 then uses these optimum error thresholds when comparing test and reference image data to achieve improved defect detection.

ADC system 20 includes a workstation 30 that supports both a laser imaging system (LIS) and the ADC process. The LIS conventionally includes confocal optics 50, a display 60, and an X-Y-Z translation stage 70, and is configured to image a reference surface. In FIG. 1 that reference surface is a surface of a semiconductor wafer 80. For a more detailed discussion of an LIS for use in the present invention, see the above-incorporated patent entitled "Laser Imaging System For Inspection and Analysis of Sub-Micron Particles."

Figure 2A:
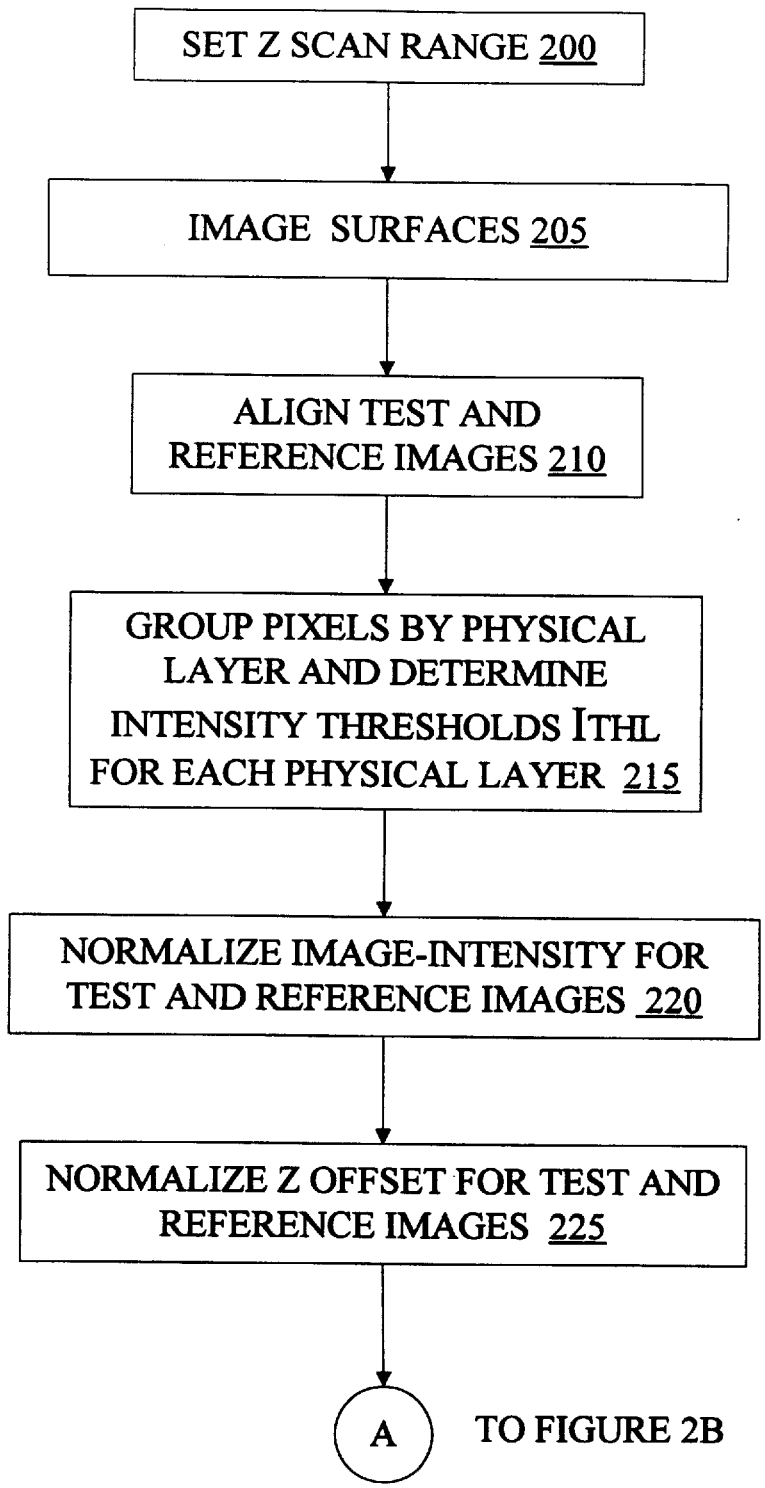
FIGS. 2A and 2B combined are a flowchart depicting an ADC process in accordance with the present invention.
Figure 2B:
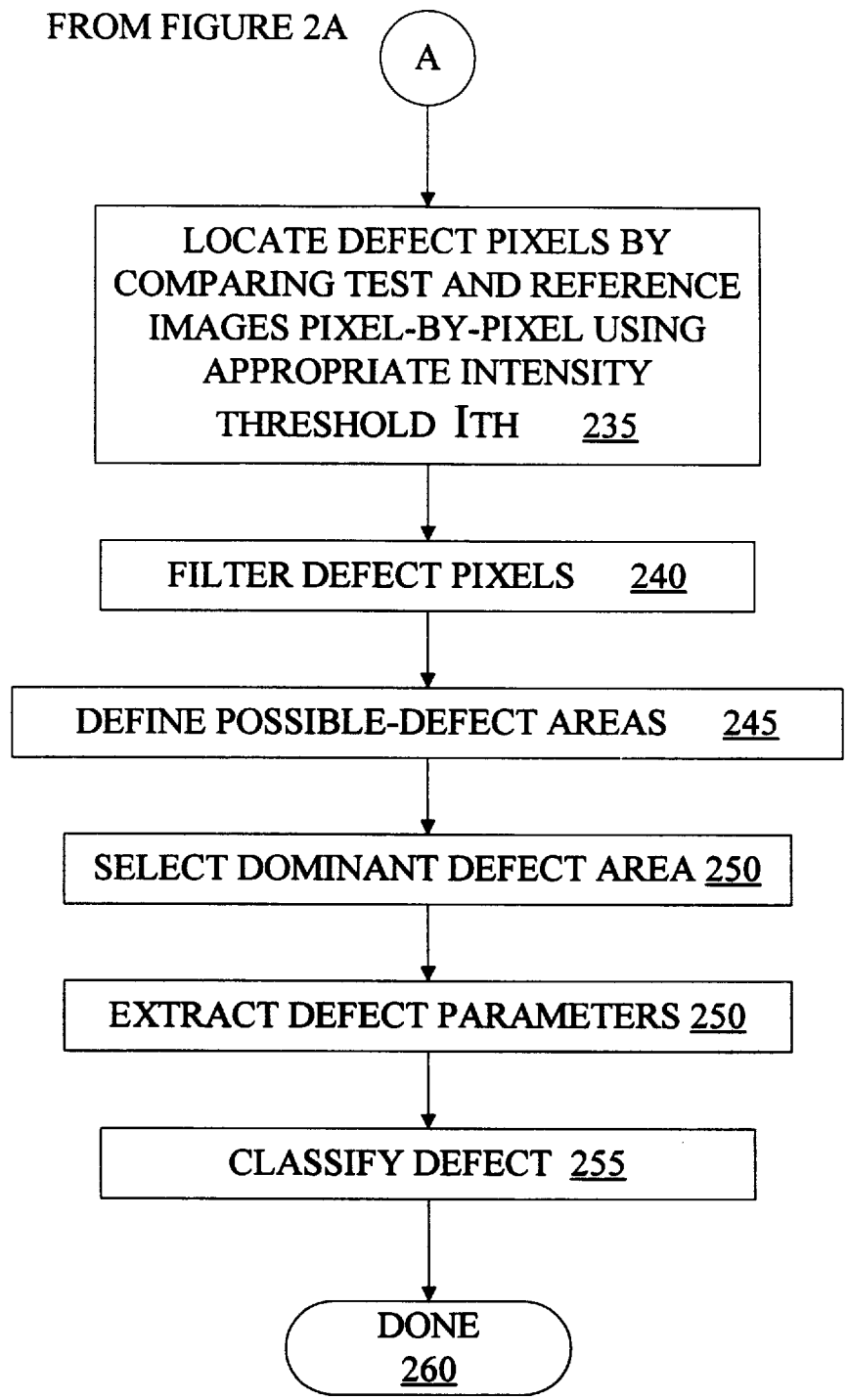

FIGS. 2A and 2B combined are a flowchart depicting an ADC process in accordance with the present invention. Beginning at step 200, ADC system 20 scans the test surface (e.g., the surface identified as including one or more defects) to establish the appropriate Z-scan range and image intensity. It is preferred to establish the Z-scan range using the test surface instead of the reference surface because the presence of defects may change the optimum z-scan range (e.g., a tall defect will require a greater z-scan range than a surface without defects). In one embodiment, this preliminary scan is accomplished using the set-Z function described in the above-identified application entitled "Automated Surface Acquisition For a Confocal Microscope," which is incorporated by reference.

Having established an appropriate z-scan range and image intensity, three-dimensional images of the test and reference surfaces are obtained (step 205) using confocal optics 50, preferably of a laser-based confocal microscope. The following describes the process of obtaining an image using a confocal microscope, and is applicable to both test and reference images.

Next, in step 210, ADC system 20 aligns the test and reference images in the x-y plane. The imaging and alignment processes of step 210 are conventional. For more information regarding conventional alignment and image acquisition, see the above-referenced application entitled "Method for Characterizing Defects on Semiconductor Wafers."

To obtain an image of a surface using confocal optics 50, a beam of light passes through an objective lens and is scanned across the surface from a number of locations along the z axis. The scanned laser beam generates a number of signals at each z location, each of the signals representing an intensity of light reflected through the objective lens from a given point on the surface. The group of signals provided by an x-y scan from a single z location of the objective lens is called a "slice" of intensity data. Slices taken from a number of locations along the z axis overlap to form a three-dimensional set of reflected intensity data, hereafter referred to as a "volumetric data set."

A pair of surface arrays, $S_I$ and $S_Z$, may be derived from a volumetric data set extracted by a confocal microscope by determining, for each x-y coordinate, the maximum intensity value, $I_{max}$, and the Z coordinate corresponding to the maximum intensity value. (For simple reflective surfaces, the confocal response of the LIS is a maximum at the surface.) The surface-intensity array $S_I$ may be represented as:

$S_I(x, y, I_{max})$ and the array of z coordinates corresponding to the maximum intensity values may be represented as:

$S_Z(x, y, Z_{Imax})$, where $Z_{Imax}$ represents the Z coordinate corresponding to the point of maximum reflected intensity for a given x-y coordinate.

In one embodiment, surface arrays $S_I$ and $S_z$ are updated as the ADC system scans the test surface from each Z position. Each intensity value of each slice of intensity data is compared to a maximum intensity value corresponding to the same x-y coordinate in the array of maximum intensity values. If the intensity value of the slice is greater than the corresponding maximum intensity value, then the intensity value of the array of maximum intensity values, $S_I(x, y, I_{max})$, is updated with a new maximum intensity value for that x-y coordinate and the array of Z values, $S_Z(x, y, Z_{Imax})$, is updated with the Z location of the new maximum intensity value. Because the point of maximum reflected intensity gives an indication of the location of the surface, the array of Z values $S_Z$ provides an indication of the surface contour. This second method is faster and requires less memory than is required for generating a complete volumetric data set. The arrays $S_I$ and $S_Z$ collectively represent image pixels in three dimensions. Hereafter, the term "pixel" refers to a single x-y location corresponding to both array $S_I$ and array $S_Z$.

For a more detailed description of a laser imaging system that employs a confocal microscope, see the copending application entitled "Laser Imaging System For Inspection and Analysis of Sub-Micron Particles," the content of which is incorporated herein by reference.

Different physical layers of a given surface are typically of different types of materials, and therefore exhibit different image properties. For example, different layers on a semiconductor substrate may be due to layers of pure silicon, silicon dioxide, metals, or photoresist. In addition to differences in image intensity, different materials exhibit differences in image "texture." For example, some materials, such as pure silicon, produce "smooth" images, which have relatively consistent intensity values from pixel to pixel; other materials, such as aluminum, produce "rough" images, which vary in intensity from one pixel to the next.

Recall that defects are detected by aligning test and reference images and then subtracting the images one from the other. Intensity differences between corresponding test and reference pixels that exceed an intensity-error threshold indicate the presence of a defect. When the pixels being compared are of a smooth portion of an image, the difference in intensity will, in the absence of defects, be relatively small. Thus, the intensity-error threshold should be made small to achieve the appropriate balance between sensitivity and selectivity. On the other hand, corresponding pixels in rough areas of test and reference images have far greater intensity differences in the absence of a defect. Thus, the error threshold should be greater than that for smooth images.

ADC system 20 takes advantage of the different image properties of different layers by separately analyzing the image properties of each layer to establish an optimum intensity-error threshold $I_{TH}$ for each layer. Thus, in step 215 ADC system 20 collects pixels having similar $Z_{Imax}$ values to separate various physical layers of the reference surface. ADC system 20 then uses the intensity data associated with each group of pixels to assign each group (and therefore each layer) an optimum intensity-error threshold $I_{THL}$. The process of grouping pixels by z value identify physical layers and assigning each layer an optimized intensity-error is described in detail in connection with FIGS. 3A and 3B.

Images of defect-free areas of the test surface should be very similar to images of corresponding areas of the reference surface. In practice, however, test and reference images differ slightly in intensity even in the absence of defects due to imaging and process variations. ADC system 20 compensates for these normal intensity differences (step 220) by providing an intensity offset $I_{OFF}$ so that they do not result in the erroneous detection of defects.

The test and reference images are aligned and their relative intensities are compared pixel-by-pixel. The x-y locations of any test and reference pixel pair $P_T$, $P_R$ having intensity values $I_{MAX}$ that differ by an amount exceeding the intensity-error threshold $I_{TH}$ assigned to the x-y location are identified as potential defect pixels. The intensity differences of the remaining pixels are then used to create an intensity histogram. The peak value of the intensity histogram represents the most common intensity difference between test and reference pixel pairs $P_T$, $P_R$. In step 220 ADC system 20 compensates for normal intensity differences by offsetting the intensity values of each reference pixel $P_R(I_{max})$ by the peak value of the intensity histogram.

The Z differences of all non-defect pixels are then used to create a Z histogram, the peak value of which represents the most common Z difference between test and reference pixel pairs $P_T$, $P_R$. In step 225 ADC system 20 compensates for any z offset between the test and reference images by offsetting the z values of each reference pixel $P_R(Z_{Imax})$ by the peak value of the z histogram.

Once the test and reference images are aligned in three dimensions and normalized for intensity, the intensity values $I_{max}$ of corresponding test and reference images are compared pixel-by-pixel (step 235) using the intensity-error threshold $I_{TH}$ assigned to the z level associated with the reference pixel. The x-y locations of corresponding pixels having intensity values $P_T(I_{max})$ and $P_R(I_{max})$ that differ by an amount exceeding the intensity-error threshold $I_{TH}$ are stored in memory as an array of potential defect pixels (the defect array D). In one embodiment, the defect array D is represented in memory using a single binary bit for each pixel: a logic one or a logic zero respectively represents the presence or absence of a defect at a given x-y location. Alternatively, a defect array may be represented in memory using multiple bits to store the intensity and/or Z difference associated with each defect pixel.

In step 240 the defect array D is filtered to reduce noise. One embodiment of ADC system 20 employs a local-alignment filter. First, the local-alignment filter compares each of the intensity $P_R(I_{max})$ of each reference-image pixel with the intensity $P_T(I_{max})$ of each test-image pixel. If the difference between the two intensities exceeds the appropriate intensity-error threshold $I_{TH}$, then the intensity of the reference pixel $P_R(I_{max})$ is compared to the intensity of one of the test-image pixels adjacent to the corresponding test-image pixel. If the difference between those two pixels exceeds the threshold $I_{TH}$, then the intensity of the reference pixel $P_R(I_{max})$ is compared with the intensity of another one of the test-image pixels adjacent to the corresponding test-image pixel. Only if the intensity difference between the reference-image pixel and the corresponding test-image pixel and the differences between the reference-image pixel and each of the adjacent test-image pixels exceed the threshold is the test-image pixel identified as a potential defect pixel $P_D$. The local-alignment filter thus corrects for minor alignment errors.

ADC system 20 may also employ an image-density filter to further reduce noise. The image-density filter examines the area surrounding a potential-defect pixel $P_D$ to determine the density of potential-defect pixels in the area. High-densities indicate the presence of a defect, while low densities are dismissed as random noise.

In another embodiment, those defect pixels lying on a feature edge or on a grainy (rough) layer are filtered further. In that embodiment, a potential-defect pixel is deemed non-defective if (1) the adjacent pixel below and to the right of the defect pixel is not labeled a potential defect; and (2) at least one of the adjacent pixels to the right or below the potential-defect pixel is not labeled a potential defect.

After filtering, the remaining potential-defect pixels $P_D$ are clustered (step 245) using conventional techniques such as dilation and erosion. While such techniques work well, they can be slow. Thus, some embodiments of the invention take advantage of modified dilation and erosion techniques that locate defect boundaries faster than do conventional techniques. Those techniques are described in a commonly owned copending U.S. patent application entitled "Ring Dilation and Erosion Techniques for Digital Image Processing," by Ke Han and Ken K. Lee, application Ser. No. 08/757,490, filed herewith, which is incorporated herein by reference.

The boundaries of potential defects are conventionally represented by a list of connected pixels (each pixel is adjacent to at least two others). ADC system 20 then selects from among the potential defects a single "high level" defect for further analysis. In one embodiment, ADC system 20 calculates the area of each potential defect and selects the potential defect having the greatest area.

The area calculation used is preferably not a simple two-dimensional calculation, but instead includes a measure of intensity differences between the test and reference images in the potential defect regions. In one embodiment, a term coined "base area" refers to sum of the intensity differences between each corresponding pair $P_T$, $P_R$ of test and reference pixels within a given potential defect area.

The area calculation can be further weighted in favor of potential defects that occur near the center of the test image. Defects are more likely to occur in the center because the center reflects the coordinate given ADC 20 by the defect scanner. Depending upon the position accuracy of translation stage 70 (FIG. 1), a radius is defined within which the defect is almost certain to reside. ADC system 20 then measures, for each potential defect, the distance between the center of the potential defect and the center of the test image. This distance is then subtracted from the radius to provide an indication of how far each potential defect is from the image center. The difference values so obtained are normalized, multiplied by a weighting factor and the base area of each potential defect, and then added to the base area. The resulting "weighted" base area favors potential defects that occur near the center of the test image.

The base areas of potential defects may be further weighted to compensate for differences in image texture. Inherent intensity variations of grainy areas increase the likelihood that a potential defect detected in a grainy region is not an actual defect. Thus, in one embodiment ADC system 20 reduces the base area of potential defects located in areas corresponding to relatively grainy regions of the reference surface and increases the base area of potential defects located in areas corresponding to relatively smooth regions of the reference surface.

ADC system 20 uses an intensity-threshold lookup table for texture weighting. In an embodiment of the invention that acquires images that include 64 image slices, the intensity-threshold lookup table includes 64 entries, one for each slice. Each entry stores the intensity threshold $I_{TH}$ for a given slice (i.e., for a given value of $Z_{Imax}$). The appropriate intensity threshold $I_{TH}$ for a given pixel may then be looked up by applying the Z-value $P_R(Z_{Imax})$ of the pixel to the intensity-threshold lookup table.

ADC system 20 looks up the intensity threshold $I_{TH}$ corresponding to the average value of $Z_{Imax}$ for the pixels within the potential defect area. That calculated intensity threshold is then compared to the midpoint between the user-defined minimum intensity threshold and the empirically derived maximum intensity threshold. If the intensity threshold corresponding to the average value of $Z_{Imax}$ for the pixels within the potential defect area is less than the midpoint, the potential defect is regarded as occupying a smooth region; consequently, the base area of such a potential defect is increased to reflect the increased likelihood that a potential defect in a smooth region is, in fact, a defect. Otherwise, the defect is regarded as a rough-region defect and the base area is decreased. The amount that the base area is increased (decreased) is in direct proportion to the difference between the calculated threshold and the midpoint threshold. Thus, if the calculated threshold is equal to the minimum (maximum) threshold, the increase (decrease) in base area is maximum. On the other hand, if the calculated threshold is equal to the midpoint threshold, the base area is left unchanged.

In one embodiment, the user can set the degree to which potential defects are weighted for texture. For example, the user may have the option of selecting texture weighting of zero, one, two, or three to assign empirically determined weights of 0, 0.75, 1.0, and 1.25, respectively. The area to be added (subtracted) is obtained by multiplying the base area by the selected weighting and the proportion by which the calculated threshold is away from the midpoint threshold.

After weighting the base areas of each potential defect as discussed above, ADC system 20 selects the potential defect having the greatest base area as a "high level" defect for further analysis. In one embodiment, the high-level defect is represented in memory as a "defect mask" that includes a single binary bit for each unique x-y location of the compared test and reference images. Pixels within the defect boundary are set to a logic one to identify the defect locations.

Having identified a single high-level defect, ADC system 20 moves on to step 250. Defect parameters are extracted from the area of the test image that corresponds to the defect mask. Such characteristics include image intensity, texture, boundary curvature, area, and shape.

For example, if area is a defect parameter, then the area within the defect boundary is assigned a magnitude conventionally expressed in a normalized form so that values run from, for example, 0 to 1 or −1 to 1. Other parameters are similarly assigned magnitudes, and these magnitudes are used to define a defect-parameter vector corresponding to the defect. Additional defect parameters may be extracted by analyzing various characteristics of the those areas of the reference image that correspond to the defect mask. For example, an otherwise "normal" looking area of the test image may be identified as defective for missing a surface feature present in the reference image.

Software for extracting defect parameters in accordance with some embodiments of the present invention is available from ISOA Incorporated of Richardson, Texas. That software may be augmented to include additional functionality as described herein.

Similar defects have similar defect-parameter vectors. In other words, two defects with similar size, shape, texture, surface curvature, etc., will have similar defect-parameter vectors, and are likely to be of the same defect type. Based on this premise, an embodiment of the present invention classifies a defect (step 255) by comparing the defect's defect-parameter vector, using conventional fuzzy-logic comparison techniques, with a knowledge base of previously stored defect vectors for different types of defects. The closest vector identifies the type of defect. An embodiment of the invention further estimates the degree of confidence in the classification based on the precision of the defect-parameter vector match. For more information pertaining to conventional comparison techniques, see pp. 414–421 of Anil K. Jain, "Fundamentals of Digital Image Processing," Prentice-Hall, Inc. (1989) and pp. 185–187of Rafael C. Gonzalez and Richard E. Woods "Digital Image Processing," Addison-Wesley (What year?), both of which are incorporated herein by reference.

Some embodiments of the invention take advantage of the z information made available by confocal optics 50 to provide additional defect parameters. These defect parameters include 1. physical roughness (small z variations) of the defect area,
2. z contrast variations (large z variations),
3. the sign of the relative z value of the defect region compared with the reference, which may be used, for example, to distinguish between pits and particles,
4. the magnitude of z values of the defect region relative to the corresponding reference region,
5. the signed average Z-difference between the test and reference image pixels within the defect boundary, and
6. surface slope, determined by relative z values of adjacent x-y locations.

The above list is illustrative and not limiting. Z information may be employed in many other ways to develop additional defect parameters. For example, one embodiment obtains yet another useful defect parameter by calculating the fraction of defect pixels within the defect boundary that extend above or below the boundaries of the layer in which they reside. To accomplish this, the z-boundaries (i.e., the top and bottom) of a layer associated with a given defect are determined from the grouping of slices discussed above in connection with FIG. 2A. The defect pixels within the defect boundary are then compared to the layer boundaries to determine whether the defect extends above or below them.

For a more exhaustive analysis, additional defect parameters, such as profile shape, may be obtained by analyzing a vertical slice of data taken through the defect so that the vertical slice represents a vertical, two-dimensional cross-section of the defect. Such a cross-section may be used to define defect parameters representing, for example, cross-sectional area and boundary features. In another embodiment, additional defect parameters are defined by providing one or more silhouettes of the defect by looking "sideways" at the defect to determine the defect profile. To ensure that only the defect is considered, only those columns of data points (i.e., data points sharing a common x-y location) within the x-y defect boundary are considered. For example, the defect may be viewed along a line parallel to the x axis from the first y location of the defect boundary to the last y location of the defect boundary. When looking at the defect from the x direction, the x element of the array is not considered.

Adding one or more of the above-listed z-based parameters to the defect vector characterizing a given defect improves the accuracy of defect classification and increases the number of types of defects that can be identified. For example, even small differences in surface height over a limited region with respect to the rest of the image can indicate buried defects of non-trivial thickness that have caused an overlying layer to bulge upward. Moreover, small surface depressions can indicate subsurface voids in prior layers.

In one embodiment, various defect parameters are used to detect the presence of potential open or short circuits. Conductors on integrated circuits are typically formed of specular materials such as aluminum. Consequently, conductors typically exhibit relatively high maximum reflected intensity values $I_{MAX}$. Thus, ADC system 20 can be configured to identify the absence of specular material between specular elements as a potential open circuit, or the presence of additional specular material between specular elements as a potential short circuit.

Figure 3A:
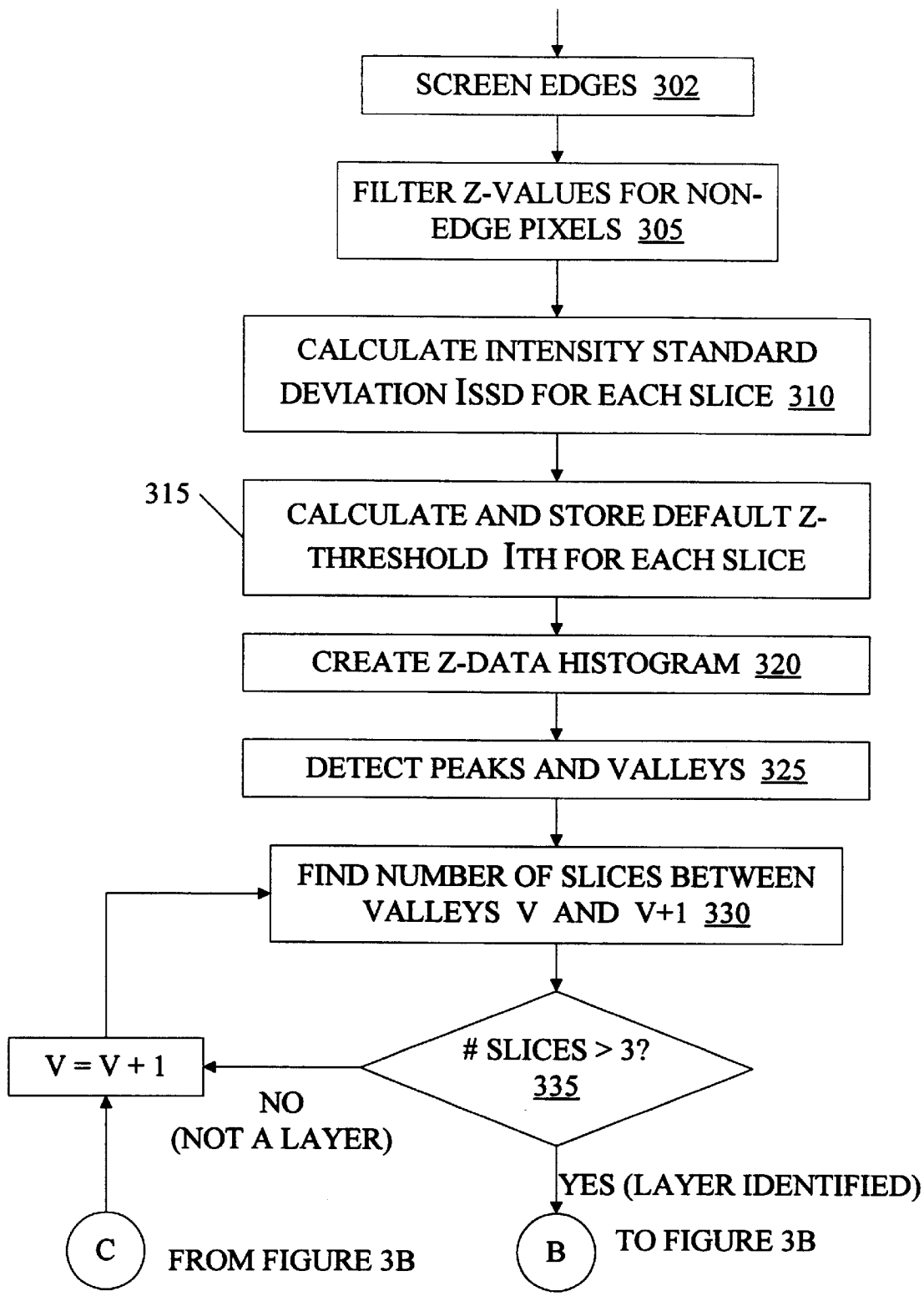
FIGS. 3A and 3B combined are a flowchart depicting the process of establishing multiple error thresholds $I_{TH}$ for a multi-layer reference surface (step 215 of FIG. 2A)
Figure 3B:
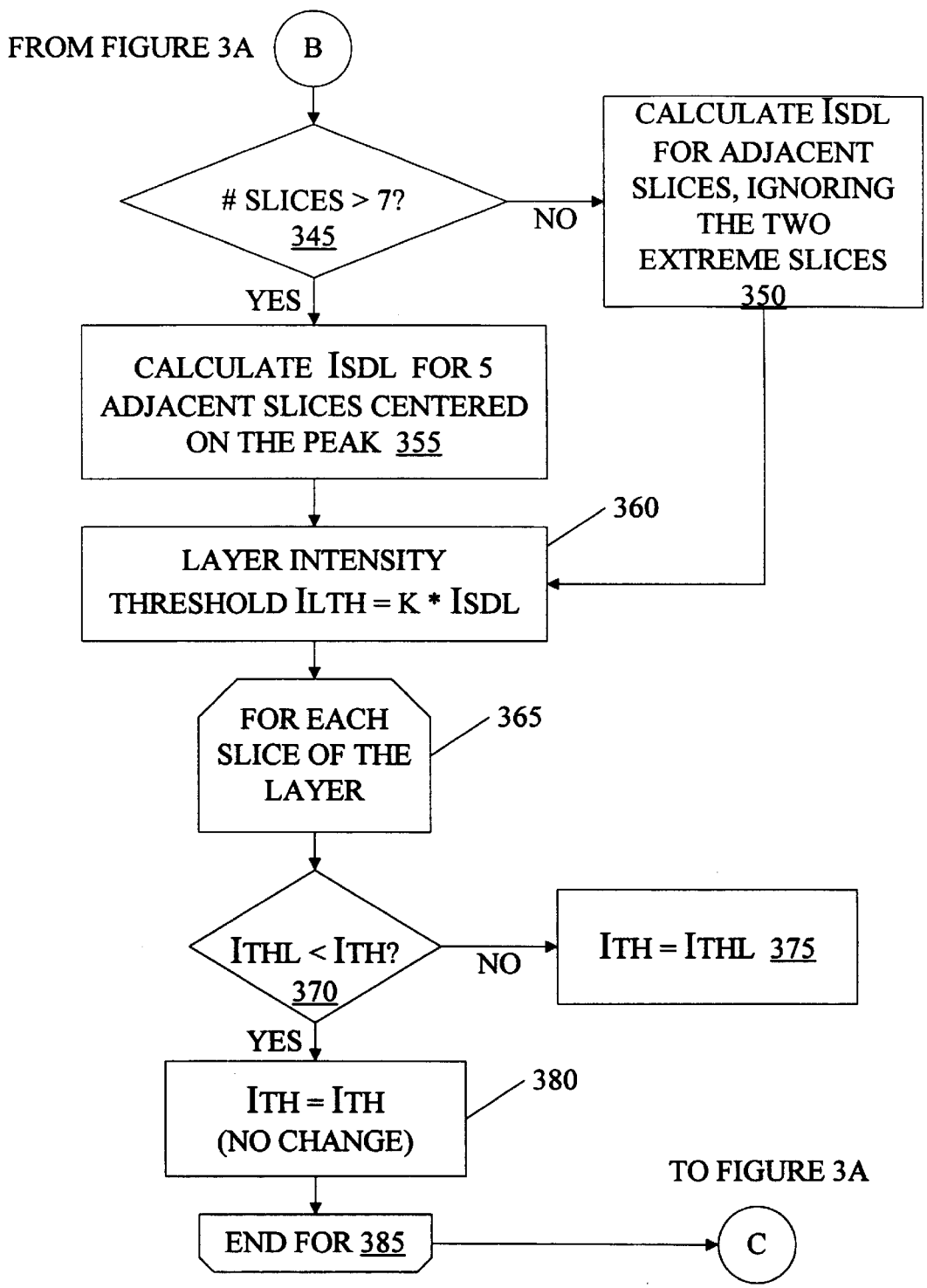

FIGS. 3A and 3B combined are a flowchart depicting the process of establishing multiple error thresholds $I_{TH}$ for a multi-layer reference surface (step 215 of FIG. 2A). Beginning with step 300, ADC system 20 screens the pixels of the reference image that correspond with the edges of physical features of the reference image. This screening, or filtering, is used because edge data is typically very noisy in Z.

Edge pixels are typically of much lower intensity than are pixels representing other surface features, with pixels at the center of edges being particularly dark. ADC system 20 uses this attribute to identify edge pixels. In one embodiment, pixels having an intensity value $I_{MAX}$ less than an empirically derived maximum central edge intensity are identified as central edge pixels.

Having identified the central edge pixels, ADC system 20 selects each central edge pixel and determines the edge gradient direction (i.e., the direction perpendicular to the direction of the edge in which the central edge pixel resides) using conventional edge gradient detection techniques. ADC system 20 examines the intensity values associated with a chain of up to seven sequential pixels extending from the central edge pixel in the direction of the edge gradient. Starting with the pixel closest to the identified central edge pixel and continuing until the intensity value of one of the chain of pixels exceeds an empirically derived maximum edge intensity. Each pixel of the chain is identified as a possible edge pixel. Then, to further discriminate edges, those pixels adjacent to possible edge pixels are identified as near-edge pixels.

Intensity thresholds $I_{TH}$ can vary between the user-defined minimum intensity threshold and the empirically derived maximum threshold. Each identified edge pixel is assigned a default intensity threshold $I_{DTH}$, which is the midpoint between the minimum and maximum intensity thresholds. The default intensity threshold $I_{DTH}$ is then stored, along with a corresponding default Z level, as one of the intensity thresholds $I_{TH}$ in the intensity-threshold lookup table. The value $Z_{Imax}$ associated with each edge pixel is then assigned the default Z level. An exemplary default Z level is associated with an extreme slice, such as slice zero, that does not include image data.

The improved edge detection provided by embodiments of the invention may be used to provide additional defect parameters. In one embodiment, each reference pixel $P_R$ having an intensity value below an empirically derived probable-edge intensity is identified as a probable edge pixel. For each probable edge pixel the corresponding test pixel $P_T$ and the eight test pixels adjacent to the corresponding test pixel are examined. If none of those test pixels is a possible edge pixel (i.e., does not exceed the empirically derived maximum edge intensity), then the test pixel $P_T$ corresponding to the reference pixel $P_R$ is marked as a defect pixel $P_D$. However, if any of those pixels is a possible edge pixel, then no defect is detected.

A similar approach is used in one embodiment to detect extra edges on the test surface. If a test pixel $P_T$ is identified as a probable edge pixel, then the corresponding reference pixel $P_R$ and the eight reference pixels adjacent to the corresponding reference pixel are examined. If none of those reference pixels is a possible edge pixel, then the test pixel $P_T$ corresponding to the reference pixel $P_R$ is marked as a defect pixel $P_D$. However, if any of those reference pixels is a possible edge pixel, then no defect is detected.

In another embodiment, lines within the defect boundary on the test image are detected using conventional line-detection and line-following techniques. ADC system 20 calculates the distance between the starting and ending points of each line within the defect area. If the distance is less than or equal to two pixels, then the line is marked as closed curve; otherwise, the line is marked as an open curve. This information may be used to establish further defect parameters, such as the numbers of closed and open curves and the average lengths of the curves.

In step 305 the Z values of the non-edge pixels (those pixels not identified as edge pixels or near-edge pixels) are filtered by replacing each observed z-value with a filtered z-value equal to the average of the observed z-value and the eight observed z values of the adjacent pixels (i.e., the z-value of each pixel is replaced with an average of the z values from a three-by-three matrix of pixels centered on the selected pixel). Of course, other types of filtering may also be used, as will be apparent to those of skill in the art.

Next, in step 310 ADC system 20 calculates the standard deviation of the intensity values for each slice ($I_{SSD}$). Each slice-intensity standard deviation ISSD is then multiplied by a constant K (e.g., K=2.75 in one embodiment) and stored in the intensity-threshold lookup table as an intensity-error threshold $I_{TH}$ (step 315).

In accordance with one embodiment of the invention, pixels of the reference image are grouped according to their respective z values $P_R(Z_{Imax})$ to identify different physical layers of the reference surface. Because different layers of a surface typically have different image properties, such as reflectance and image texture, the groups of pixels are analyzed separately to determine an optimum intensity-error threshold $I_{TH}$ for each of the groups, and therefore for each layer of the reference surface. This aspect of the present invention is illustrated with reference to FIGS. 4A and 4B.

Figure 4A:
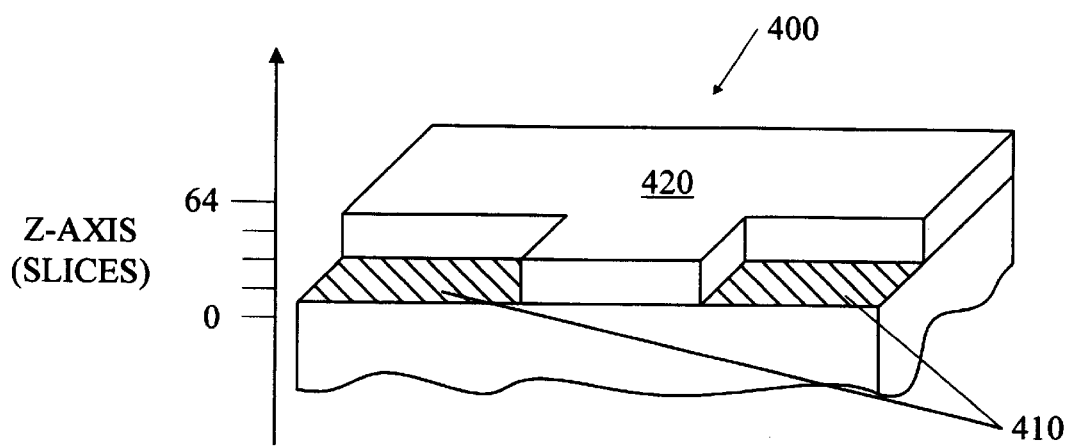
FIG. 4A is a perspective view of a portion of a silicon wafer 400 having a rough surface 410 partially overlaid with a material having a relatively smooth surface 420.
Figure 4B:
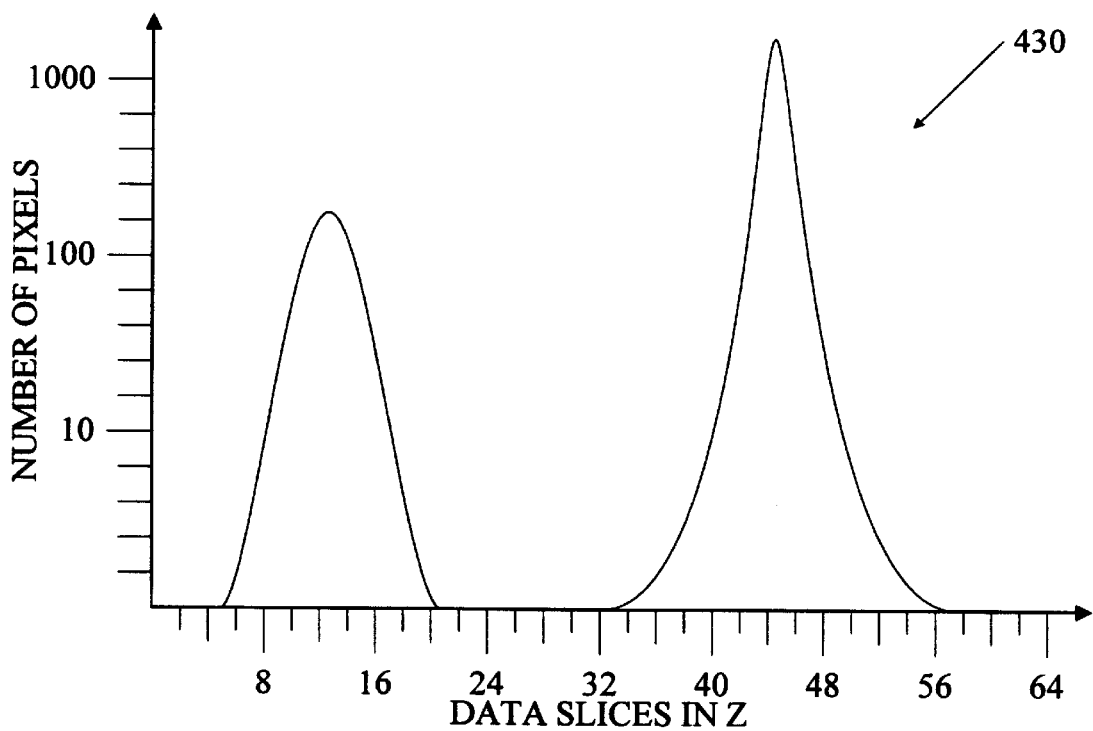
FIG. 4B is a histogram 430 depicting the number of pixels (the number of maximum intensity values $I_{\lambda max}$) for each of 64 "slices" of intensity data.

FIG. 4A is a perspective view of a portion of a silicon wafer 400 having a rough surface 410 partially overlaid with a material having a relatively smooth surface 420. FIG. 4B is a histogram 430 depicting the number of pixels (the number of maximum intensity values $I_{\lambda max}$) for each of 64 "slices" of intensity data. Because the maximum intensity values $I_{max}$ occur when the focal point of confocal optics 50 is coincident with a surface, elevations (slices) associated with a large number of maximum intensity values $I_{max}$ indicate the presence of a surface. In the example of FIGS. 4A and 4B, the two surface layers of wafer 400 are indicated by corresponding peaks of histogram 430.

Histogram 430 is for illustrative purposes. Histograms derived from actual surfaces are typically noisy. Thus, empirically derived histograms are smoothed using conventional techniques. For example, in one embodiment the number of pixels in each slice is replaced with an average of the number of pixels of that slice and the two adjacent slices.

Returning to FIG. 3A, in step 325 ADC system 20 detects the peaks and valleys of the smoothed histogram 430. In one embodiment, a peak is a slice in which the number of pixels is greater than the number of pixels in either adjacent slice, and a valley is a slice in which the number of pixels is fewer than the number of pixels in either adjacent slice. Other schemes may also be used, as will be apparent to those of skill in the art.

Peaks and valleys may be due to noise or to physical features of the reference surface. Some noise is filtered out by requiring the number of pixels in a given slice be greater than a predetermined threshold number before that slice be considered a peak or a valley. In one embodiment ADC system 20 assigns the user-defined minimum intensity threshold to slices having fewer than 50 pixels. Slices having more than 100 pixels are assigned the intensity threshold $I_{SSD}$ derived in step 310. Finally, slices having between 50 and 100 pixels are assigned an intensity threshold linearly interpolated between the minimum intensity threshold and the intensity threshold $I_{SSD}$. For example, a slice having 75 pixels (i.e., midway between 50 and 100) would be assigned an intensity threshold $I_{TH}$ midway between the minimum intensity threshold and the intensity threshold $I_{SSD}$.

Physical layers are further distinguished from noise by requiring a layer be identified by some minimum number consecutive slices between valleys. In the example of FIG. 3A, if the number of slices between valleys is less than three, then the process moves on to the next pair of valleys (decision 335); conversely, if the number of slices between valleys is greater than three, then the process moves on to decision 345 of FIG. 3B.

If a surface layer is between four and seven slices (as indicated by a peak of histogram 430), ADC system 20 calculates the standard deviation of the intensity values $I_{max}$ associated with the pixels of those slices, ignoring the two extreme slices (step 350). For example, if there are five slices between valleys, the standard deviation of the intensity values is calculated for all of the pixels of the middle three slices. If the layer is greater than seven slices, then the standard deviation is calculated for the five adjacent slices centered on the slice between the selected valleys having the highest number of pixels (step 355).

Whether from step 350 or 355, the intensity standard deviation of the pixels in the detected layer is denoted ISDL. The intensity-error threshold $I_{THL}$ for the layer (for each slice identified as representing a physical layer) is calculated by multiplying the constant K (e.g., 2.75) by ISDL (step 360). Next, the layer intensity threshold $I_{THL}$ is compared (step 370) with the intensity-error threshold $I_{TH}$ previously assigned to those slices in step 315. If the layer intensity-error threshold $I_{THL}$ is greater than the previously obtained intensity-error threshold $I_{TH}$, then the intensity-error threshold $I_{TH}$ is updated (i.e., $I_{TH}$ is set equal to $I_{THL}$ in step 375); conversely, if the layer intensity-error threshold $I_{THL}$ is less than or equal to the intensity-error threshold $I_{TH}$, then the intensity-error threshold $I_{TH}$ is retained for subsequent pixel comparisons (step 380). A block 385 represents the end of the loop begun in block 365, after which the process moves to block 340 of FIG. 3A. The process continues thus until each peak of histogram 430 is analyzed.

Figure 5:
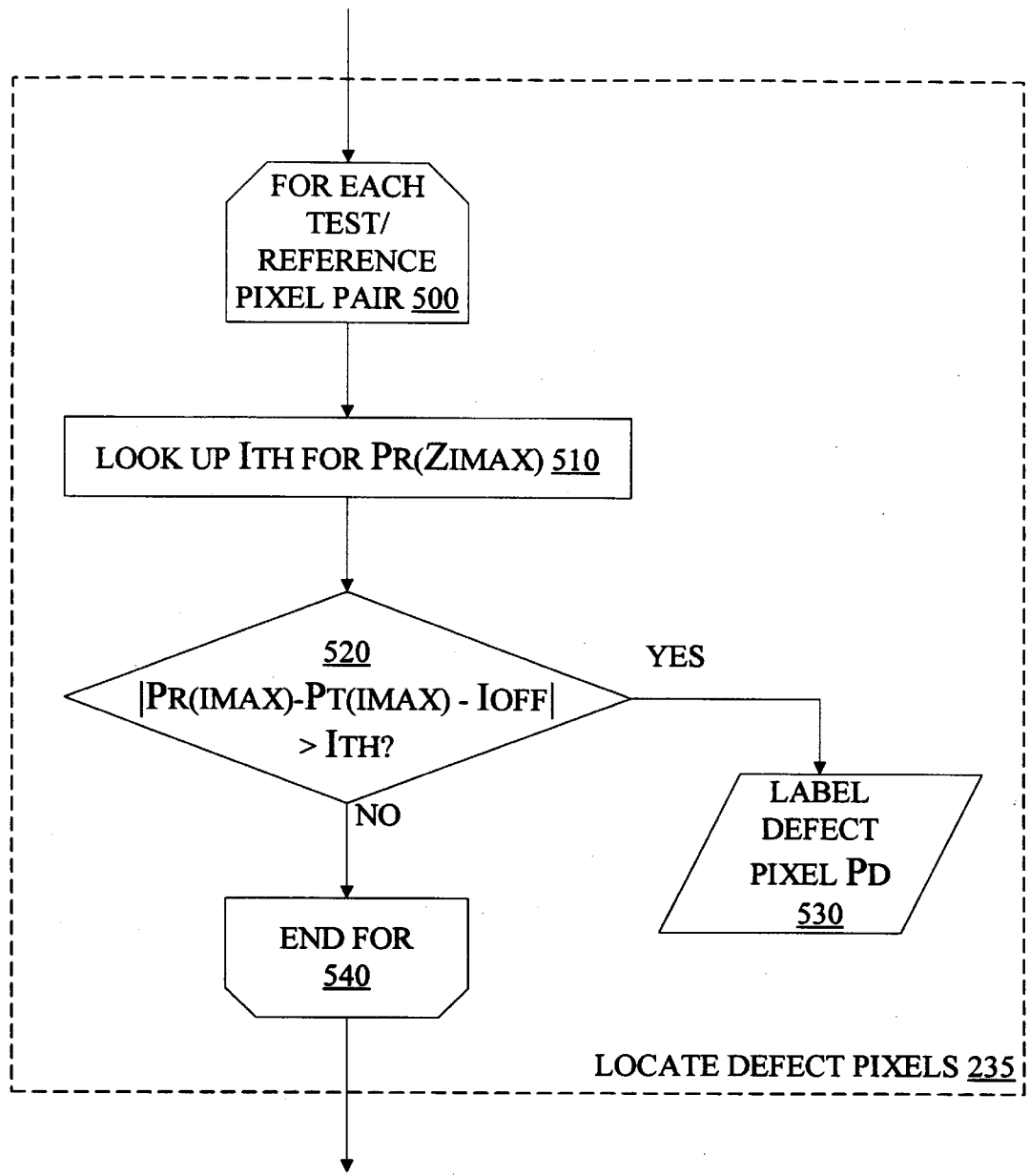
FIG. 5 is a flowchart depicting the process of locating defect pixels by comparing test and reference images (step 235 of FIG. 2B).

FIG. 5 is a flowchart depicting the process of locating defect pixels $P_D$ by comparing test and reference images (step 235 of FIG. 2B). The intensity of each reference pixel $P_D(I_{MAX})$ is compared with the intensity of the corresponding test pixel(same x-y coordinate). The comparison process uses the array of intensity-error thresholds $I_{TH}$ derived as described above in connection with FIGS. 3A and 3B.

Recall that each test pixel $P_T$ and each reference pixel $P_R$ includes a value $Z_{Imax}$ indicating to which slice that pixel belongs (or, for edge pixels, indicating a default z value). Recall also that the intensity-threshold lookup table correlates each image slice with an appropriate intensity-error threshold $I_{TH}$. ADC system 20 looks up the appropriate intensity-error threshold $I_{TH}$ for a given pixel pair $P_R$, $P_T$ using the value $P_R(Z_{Imax})$ the z location of the reference pixel $P_R$ (step 510). The threshold $I_{TH}$ obtained in step 510 for a single pixel pair $P_R$, $P_T$ is then used to compare the intensity values $P_R(I_{max})$ and $P_T(I_{max})$ of the pixel pair $P_R$, $P_T$. As discussed above with respect to step 220 of FIG. 2A, this comparison must include the intensity offset $I_{OFF}$.

In one embodiment, pixel-intensity comparisons are accomplished by subtraction. If the absolute value of the intensity difference between a pair of test and reference pixels is greater than the corresponding intensity-error threshold $I_{TH}$(i.e., if $|P_R(I_{max})-P_T(I_{max}) -I_{OFF}|>I_{TH}$), then the test pixel $P_T$ is identified as a defect pixel $P_D$ (step 530). The block 540 represents the end of the for statement of block 500.

While the present invention has been described in connection with specific embodiments, variations of these embodiments will be obvious to those of ordinary skill in the art. For example, the present invention may be applied to color images. Furthermore, the accuracy of defect detection may be improved by comparing the test image to more than one reference image. Therefore, the spirit and scope of the appended claims should not be limited to the description of the preferred versions.

What is claimed is:

1. A method comprising:

representing a three-dimensional surface, using a Cartesian coordinate system having x, y, and z axes, as a plurality of points on the surface, wherein each point is defined by an intensity value, a unique x-y coordinate, and a z coordinate specified by a z value;

collecting a first group of the points having similar z values, the first group representing a first layer of the surface;

collecting a second group of the points, each point of the second group having a z value similar to the z values of other points of the second group and dissimilar to the z values of the points of the first group, the second group representing a second layer of the surface;

determining a first error threshold for the intensity values of the first group of points; and determining a second error threshold for the intensity values of the second group of points.

2. The method of claim 1, further comprising:

representing a second three-dimensional surface as a second plurality of points on the second surface, wherein the second plurality of points is represented by a set of intensity values and a set of x-y coordinates; and aligning the x-y coordinates of the first-mentioned plurality of points with the x-y coordinates of the second plurality of points such that each of the first plurality of points corresponds with one of the second plurality of points;

determining, for each of the points in the first group, whether the intensity value of the point differs from the intensity value of the corresponding one of the second plurality of points by an amount greater than the first error threshold; and determining, for each of the points in the second group, whether the intensity value of the point differs from the intensity value of the corresponding one of the second plurality of points by an amount greater than the second error threshold.

3. The method of claim 2, wherein points in the first group that have an intensity value that differs from the intensity value of the corresponding one of the second plurality of points by an amount greater than the first error threshold are identified as difference pixels, and wherein points in the second group that have intensity values that differ from the corresponding one of the second plurality of points by an amount greater than the second error threshold are also identified as difference pixels.

4. The method of claim 3, further comprising grouping neighboring difference pixels within a difference boundary, the difference boundary defining an defect area that includes a potential defect on at least one of the first and second surfaces.

5. The method of claim 4, further comprising extracting defect parameters from the defect area.

6. The method of claim 5, wherein the defect parameters include at least one of the size, shape, and reflectivity of the defect area.

7. The method of claim 4, wherein defining the defect area includes dilating the neighboring difference pixels.

8. The method of claim 7, wherein dilating the neighboring difference pixels includes forming a ring of radius R around each of the neighboring difference pixels.

9. The method of claim 7, wherein defining the defect area includes eroding the dilated neighboring difference pixels.

10. A method of locating defects on a test surface, wherein the test surface is contained within a test volume represented by a Cartesian coordinate system having x, y, and z axes describing a set of unique x-y-z coordinates, the method comprising the steps of:

scanning the test surface in the test volume with a focused beam so that the focal point of the focused beam coincides, in turn, with each unique x-y-z coordinate within the test volume;

determining, for each column of points specified by a unique x-y coordinate in the test volume, a maximum reflected intensity value of the focused beam;

determining, for each column of points specified by a unique x-y coordinate in the test volume, a Z value corresponding to the maximum reflected intensity value of the focused beam;

storing all the Z values to form an array of test data representing a three-dimensional image of the test surface; and comparing the array of test data with an array of reference data to identify elevational differences between the array of test data and the array of reference data.

11. The method of claim 10, further comprising comparing the differences between the array of test data and the array of reference data with defect data indicative of different defect types.

12. The method of claim 10, wherein the elevational differences are described as an average Z-difference of a defect area on the test surface.

13. The method of claim 10, wherein the elevational differences are described as a fraction of a first number of points imaged on the test surface that extend above a selected physical layer of the test surface over a second number of points imaged on the test surface that extend below the selected physical layer of the test surface.

14. A defect characterization system comprising:
- a microscope configured to obtain a three-dimensional image of a surface, the image including a plurality of pixels each of which is expressed an intensity value and x, y, and z coordinates of a Cartesian coordinate system;
- means for collecting a first group of the pixels having similar z coordinates, the first group representing a first physical layer of the surface;
- means for collecting a second group of the pixels, each pixel of the second group having a z coordinate similar to the z coordinates of other pixels of the second group and dissimilar to the z coordinates of the pixels of the first group, the second group representing a second physical layer of the surface;
- means for determining a first error threshold for the intensity values of the first group of pixels; and
- means for determining a second error threshold for the intensity values of the second group of pixels.

* * * * *